United States Patent [19]

Pourprix

[11] Patent Number: 5,592,096
[45] Date of Patent: Jan. 7, 1997

[54] ELECTRICAL MOBILITY SELECTOR OF CHARGED PARTICLES

[75] Inventor: Michel Pourprix, Nontlhéry, France

[73] Assignee: Commissariat a l'Energie Atomique, Paris, France

[21] Appl. No.: 438,708

[22] Filed: May 11, 1995

[30] Foreign Application Priority Data

May 24, 1994 [FR] France .................................. 94 06273

[51] Int. Cl.⁶ .............................................. G01N 27/60
[52] U.S. Cl. .......................................... 324/452; 324/457
[58] Field of Search .................................. 324/452, 453, 324/457, 464

[56] References Cited

U.S. PATENT DOCUMENTS

| | | | |
|---|---|---|---|
| 2,669,665 | 2/1954 | Annis et al. | 324/452 X |
| 4,117,715 | 10/1978 | Hoenig | 324/452 X |
| 4,321,546 | 3/1982 | Schneider, Jr. | 324/452 X |
| 4,387,369 | 6/1983 | Klein et al. | 324/464 X |
| 4,502,012 | 2/1985 | Rush | 324/452 |
| 4,556,849 | 12/1985 | Kalakutsky et al. | 324/464 |
| 5,117,190 | 5/1992 | Pourprix | 324/452 |

FOREIGN PATENT DOCUMENTS

| | | |
|---|---|---|
| 0404681 | 12/1990 | European Pat. Off. . |
| 93/07465 | 4/1993 | WIPO . |

OTHER PUBLICATIONS

Transactions of the IEEE on Nuclear Science, vol. NS–19, No. 1, Feb. 1, 1972, pp. 64–74, Raabe, "Instruments and Methods for Characterizing Radioactive Aerosols' Electrostatic Samplers". pp. 66–67.

Database WPI, Week 8440, Nov. 14, 1984, Derwent Publications Ltd., London, GB; AN 84–248832 & SU–A–1 071 947 (Len.Aviation Inst.) Feb. 7, 1984.

Aerosol Science and Technology, vol. 13, Oct. 1, 1990, pp. 230–240, Wang et al., "Scanning Electrical Mobility Spectrometer"., pp. 232–235.

Journal of Aerosol Science, vol. 6, Dec. 1, 1975, pp. 443–451, Knutson et al., "Aerosol Classification By Electric Mobility, Etc.".

Review of Scientific Instruments, vol. 51, No. 8, Aug. 1, 1980, pp. 1098–1104, Schowengerth et al., "A Parallel Plate Electrostatic Size Classifier, Etc.".

Primary Examiner—Kenneth A. Wieder
Assistant Examiner—Diep Do
Attorney, Agent, or Firm—Pearne, Gordon, McCoy & Granger

[57] ABSTRACT

This electrostatic selector of aerosol particles of an atmosphere has a first (18) and a second (20) parallel, spaced, coaxial conductive disks, between which is established an electric field, an annular slot (22) made in the first disk for communicating with the atmosphere to be examined, a central intake (26) for bringing about a circulation from the periphery of the disks of a stable, centripetal, laminar filtered air flow, an annular or circular opening (28) made in the second disk, a third disk (32) facing the second disk, means for injecting between the second and third disk, from the periphery thereof, a radial, laminar, filtered air flow, a central pipe fixed to the third disk by which the particles having the requisite electrical mobility (or the requisite dimension if the electric charge is known) are brought to the outside of the apparatus.

4 Claims, 3 Drawing Sheets

ELECTRICAL MOBILITY SELECTOR OF CHARGED PARTICLES

TECHNICAL FIELD

The present invention relates to a charged particle, electrical mobility selector more particularly used for selecting particles of a given grain size (monodisperse aerosol) from particles of a random grain size (polydisperse aerosol), which are suspended in air or in another gas.

Among other applications, this type of apparatus is e.g. particularly advantageously used in the field of research on aerosols, for testing the efficiency of filters, for producing calibrated particles or for studying the electrical charge of aerosols. It is more particularly suitable for submicron aerosols down to the smallest aerosol sizes, i.e. approximately 1 nanometer ($10^{-9}$ m).

PRIOR ART

One of the most frequently used means for selecting monodisperse particles is based on the fact that the aerosols all carry electrical charges equal to the unitary electrical charge or multiples thereof.

Thus, use has already been made for the selection of charged particles suspended in a gas, of electrostatic fields acting on the electrical charges which they carry. For this purpose, currently a definition is made of a fundamental notion in this field, which is that of the electrical mobility of a charged particle placed in an electrostatic field. This quantity, which defines the greatest or smallest aptitude of such a particle to undergo a deviation under the effect of this field can be represented by the following vector equation:

$$\vec{W} = Z\vec{E}$$

in which $\vec{W}$ is the drift velocity acquired by the particle under the influence of the electrical field $\vec{E}$ to which it is exposed. The proportionality coefficient Z between the two aforementioned quantities is the electrical mobility in question. As this electrical mobility is on the one hand proportional to the electrical charge of the particle and on the other inversely proportional to its diameter, it is possible to produce true selectors of particles as a function of their size if the charge law is known and consisting of subjecting particles entrained in a gaseous flow to the action of an electrical field existing between the two electrodes. Under the effect of the field, the charged particles is deposited, as a function of their sign, on one of the said electrodes and the abscissa of their deposition with respect to the direction of the gaseous flow is characteristic of their mobility in the sense that the higher said electrical mobility the nearer the abscissa of their deposition is to the origin of the gaseous flow carrying them. This leads to a spread or a separation in space of the collected particles. Following said separation, it is possible to select the particles having a certain mobility, i.e. a certain grain size if the charge law is known.

An apparatus based on this principle is described in French certificate of addition 90 02413 of 27.2.1990, published under No. 2 658 916 (U.S. Pat. No. 5,117,190), entitled "Electrostatic aerosol particle sensor and equipments incorporating the application thereof". This type of apparatus is illustrated in FIG. 1 and has two spaced, parallel, coaxial conductive disks 2, 4 between which is established a potential difference V and therefore an electrical field $\vec{E}$. The disk 2 has an annular slot 6 (radius $r_1$) by which are introduced the particles of an aerosol at a flow rate $q_1$. A central intake 8 is provided by means of which an air flow Q circulates under the effect of a pump not shown in the drawing.

The particles are entrained to a second annular slot 10 of radius $r_2$ made in the disk 4 under the combined action of a filtered air flow at the flow rate $q_0$ which is radial and laminar, established between the two disks and the electrical field E imposed between the two disks.

Through the slot 10 the air flows at a rate $q_2$ into a cylindrical box 12 fixed beneath the disk 4 which gives $Q=q_0+q_1-q_2$. The particles passing through the slot 10 have the same electrical mobility $Z=Q/\pi E(r_1^2-r_2^2)$.

In order to regulate the said electrical mobility to the desired value for each individual case, it is possible to act on the two parameters, namely the flow rate Q on the one hand and the potential difference V applied between the two coaxial, conductive disks 2 and 4.

By the cylindrical box 12 and the pipe 14, the particles can then be directed to any type of device suitable for the envisaged application, namely a particle counter to be calibrated with the thus produced calibrated particles.

This type of apparatus, like all the hitherto existing charged particle selectors, suffers from certain disadvantages if it is used for selecting particles having a nanometric size.

Firstly, the transport of such particles in the circuits of the system leads to losses by Brown scattering in the vicinity of the walls, particularly in the cylindrical box 12 and in the discharge pipe 14. For example, a 30 cm long pipe at a flow rate of 0.3 l/min by Brown scattering collects approximately 50% of the 3 nanometer particles.

Moreover, the trajectory is not the same for all the particles and consequently there is a spread of the transit time and a certain dispersion through the apparatus, which can be prejudicial in certain applications.

DESCRIPTION OF THE INVENTION

The object of the invention is to solve these problems.

It therefore relates to a selector of aerosol particles contained in an atmosphere, comprising a first and a second spaced, parallel, coaxial conductive disks, between which is established an electrical field by raising them to different potentials, the space between the two disks communicating with the atmosphere to be examined through an annular slot of radius $r_1$ made in the first disk, a central intake being provided in the first disk for bringing about the circulation in said space, from the periphery of the disk, of a stable, centripetal, laminar filtered air flow, the second disk being provided with an annular opening, characterized in that:

a third disk is positioned facing the second disk, means are provided for injecting into the space between the second and third disks, a radial, laminar, filtered air flow from the periphery of said two latter disks, a central pipe is fixed to the third disk, by which selected particles are brought to the outside of the apparatus.

Thus, in this configuration a second stage is provided with the aid of third and second disks and a "dynamic confinement" is obtained with the aid of a filtered air flow between these two disks. This flow channels the particles as from their extraction from the first stage. On passing out of the second stage, the particles are moved into a pipe ensuring their transfer to the outside, still in a laminar flow, with the special feature that they are confined in the vicinity of the centre of the flow and without contact with the walls (i.e.

without loss) and with identical trajectories (i.e. with identical transmit times).

According to an embodiment means are provided for establishing between the second and third disks an auxiliary electrical field $\vec{E}'$ making it possible to "detach" selected particles through the slot of radius $r_2$ from the surface with which they can be in contact.

According to another embodiment, the ring defining the opening made in the second disk has a zero internal diameter, i.e. the opening is reduced to a circular orifice.

Other embodiments of the invention can be gathered from the dependent claims.

BRIEF DESCRIPTION OF THE DRAWINGS

The characteristics and advantages of the invention can be better gathered from the following description relative to non-limitative, exemplified embodiments and with reference to the attached drawings, wherein show.

DETAILED DESCRIPTION OF EMBODIMENTS

Figure 1:
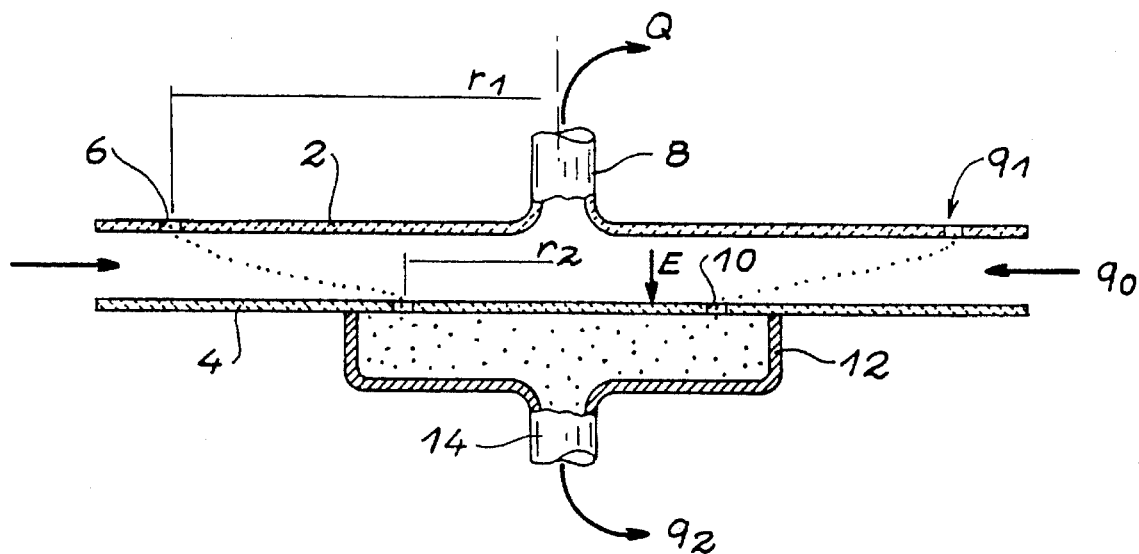
FIG. 1 prior art aerosol particle selector.
Figure 2:
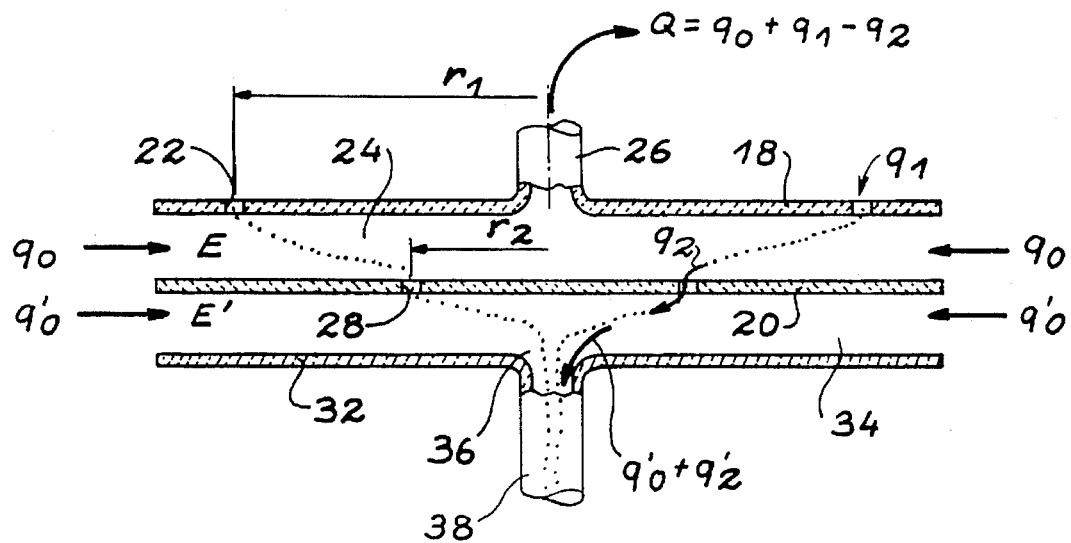
FIG. 2 The principle of a particle selector according to the invention.

FIG. 2 is a diagram of a selector according to the invention. The apparatus firstly comprises a first stage constituted by a circular electrical mobility selector (CEMS) having two concentric disks 18, 20. The first disk 18 has an annular slot 22 of radius $r_1$ by which a gas sample containing the particles to be analyzed is introduced with a flow rate $q_1$. As the two disks are conductive, it is possible to raise them in each case to a certain potential and establish an electrical field E in the space 24 separating them. In the second disk 20 is formed an annular opening 28 of mean radius $r_2$ and which will be traversed by an air flow $q_2$. Between the two disks and on the periphery of the space 24 is injected by means not shown in FIG. 2 an entrainment gas (filtered air) $q_0$, so that a laminar flow circulates between the two disks up to the central intake or suction pipe 26 which consequently absorbs a flow $Q=q_0+q_1-q_2$.

If Z is used for defining the electrical mobility of the particles, 2 h the distance separating the disks 18 and 20, V the potential difference between these disks, the theory of the apparatus shows that the aerosol particles traversing the slot of radius $r_2$ have a mobility Z such that:

$$r_2 = \sqrt{r_1^2 - \frac{2Qh}{\pi ZV}}$$

A second stage collects the particles having said same electrical mobility Z. This stage is constituted on the one hand by the already described, second disk 20 and on the other by a third disk 32 positioned facing the second disk and defining with the latter a space 34. As from the periphery of said space 34 it is possible to impose, with the aid of known means, a radial, filtered air flow rate $q'_0$, which is chosen in such a way that the air flow in said second stage is laminar. Thus, the particles selected through the opening 28 are channelled as from their extraction from the first stage.

Moreover, an electrical field E', e.g. obtained by using as the disk 32 a conductive disk and raising each of the disks 20 and 32 to a certain potential (potential difference V'), can be applied between the said two disks in order to detach the particles from the surfaces with which they could come into contact. The field E' can have a simple relationship with the field E:E'=f(E), e.g. E'=E/10. It is in particular possible to make E' dependent on E.

The third disk 32 has in its centre an opening 36 issuing onto a pipe 38. The centre of the opening 36 is preferably aligned with the centres of the disks 18 and 20, if the selected particles still flowing in laminar manner at a rate $q'_0+q_2$ and confined in the vicinity of the centre of the flow, flow in the axis of the opening 36 without contact with the walls and consequently without loss. Moreover, the trajectories followed by the particles are identical throughout the apparatus, including in the second stage and in the pipe 38, so that the particles flow with identical transit times, which are easy to determine, because the geometrical dimensions of the system are easy to determine.

The particles are then discharged by the pipe 38 to the outside of the selector.

Figure 3:
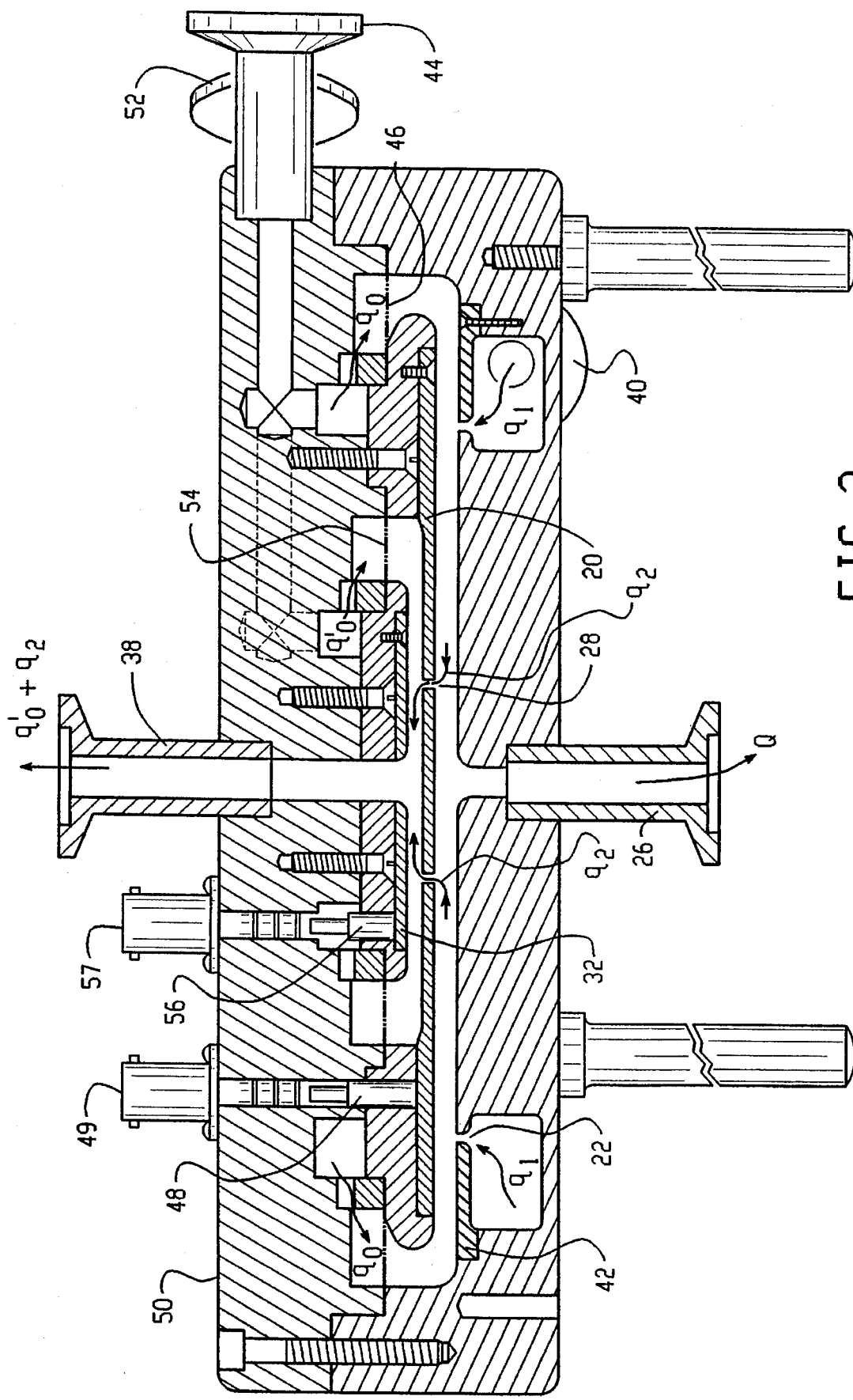
FIG. 3 A selector according to the invention in section.

An apparatus operating on the principle described hereinbefore is shown in section in FIG. 3. Use is once again made of the numerical references of FIG. 2 for the same elements.

The gas containing the charged particles to be selected returns at the flow rate $q_1$ by an end fitting 40 and passes out through the profiled slot of a lip 42.

Filtered air reenters at the flow rate $q_0$ by an end fitting 44 and passes through a porous disk 46 (fibre glass) in order to supply the first stage. It is extracted at the rate Q by the end fitting 26.

A high voltage V is applied by means of a contactor 48 and a high voltage base 49, the block 50 being at zero potential. The charged particles are also deflected from their radial trajectories and are deposited on the electrode 20 as a function of their electrical mobility.

In the second stage filtered air returns at the flow rate $q'_0$ by the end fitting 52 and passes through the porous disk 54. The gas is then sucked through the end fitting 38 at the flow rate $q'_0+q_2$.

The electrode 20 is perforated by regularly spaced holes in order to again form an annular extraction slot 28. The charged particles having the requisite electrical mobility are consequently extracted at the flow rate $q_2$ and entrained in the axis of the discharge pipe 38.

A second high voltage V' is optionally applied to the third disk 32 by means of a contactor 56 and a high voltage base 57 in order to "detach" the particles from the surface with which they are in contact.

Figure 4:
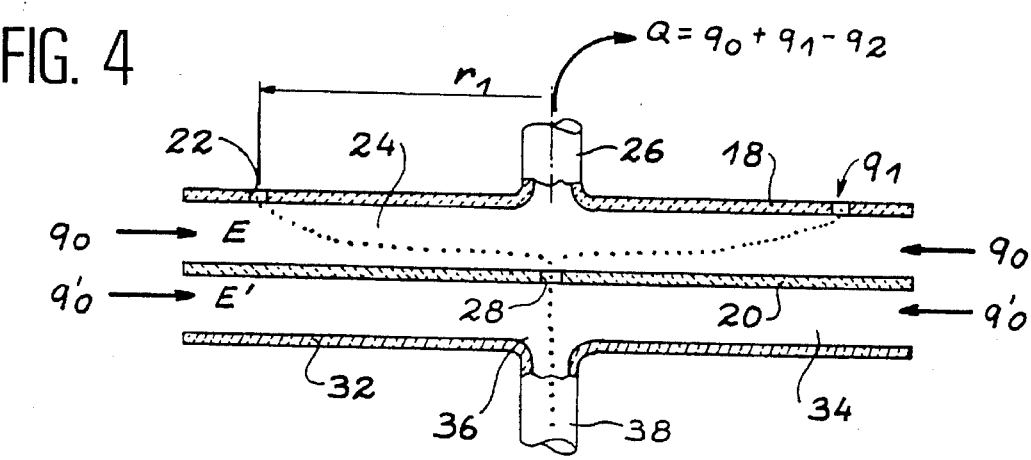
FIG. 4 An embodiment of a selector according to the invention.

More simply, the annular extraction slot 28 can be reduced to a single central, circular orifice in the manner illustrated in FIG. 4, where the numerical references have the same meaning as in FIG. 2.

Although the central extraction orifice 28 is a vital point both from the aeraulic standpoint and from the electrical standpoint, the particles deposited in the centre of the second disk are sucked up with a flow rate $q_2$ through said orifice 28. These particles have the mobility $Z=Q/\pi E r_1^2$. The diameter $\phi$ of said orifice is preferably chosen so as to ensure a good selectivity of the particles (if the diameter is large the selectivity is low), but also so as not to disturb the flow of fluid passing through the same (if the diameter is small a "jet" phenomenon occurs level with said orifice). In exemplified manner, an apparatus has been produced with $r_1$=6.5 cm and $\phi$=2.7 mm. This configuration has the advantage of not requiring an auxiliary electrical field E' and of extracting the particles precisely in the apparatus axis. Here again the particles travel in a laminar flow without contact with the walls (i.e. without loss), with identical transit times and following virtually rectilinear, identical trajectories in the second stage.

The particles are then counted by a detector 40 chosen from among known systems usually based on optical or electrical methods.

Figure 5:
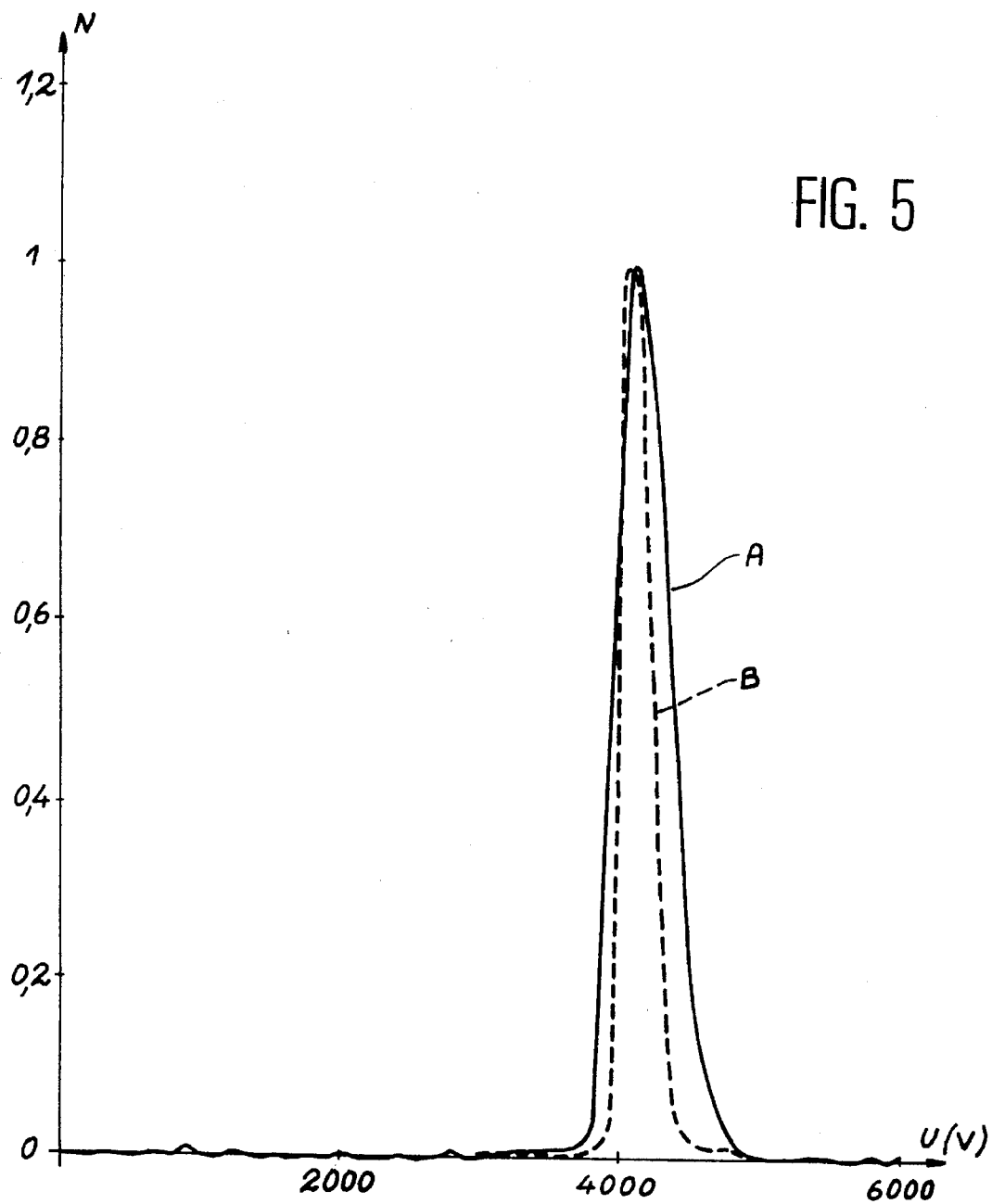
FIG. 5 Spectra obtained with a selector according to the invention.

Examples of results obtained with a selector according to the invention are shown in FIG. 5. The apparatus used is like that of FIG. 4, i.e. with a central hole 28 in the intermediate disk 20 and without electrical field E'. The selector is provided at the outlet with an optical detector (particle counter by condensation), in which the particles are entrained through a light beam and where each particle scatters a certain quantity of light, which is then analyzed by a photodetector.

Once again using the notations of FIG. 4, the characteristics for these examples are as follows:

diameter of the central extraction hole 28: 2.7 mm, distance between the disks 18 and 20: 4 mm (=distance between the disks 20 and 32), $r_1$=6.5 cm, $q_0$=20 l/min; $q_1$=$q_2$=1 l/min (curve A) or 0.5 l/min (curve B); $q'_0$=(0.4) l/min (A) or 0.9 l/min (B), diameter of particles used: 0.107 μm (particles carrying a single electrical charge), voltage V between the disks 18 and 20: variable from 0 to 600 volts.

As a function of the voltage, the curves A and B give the number N of selected particles counted per volume unit (standardized scale). These curves also show the very good resolution of the apparatus.

The apparatus described has as its essential application the production of monodisperse particles from polydisperse sources. In order to produce particles of a given size, it is merely necessary to select them as a function of the mobility Z corresponding to this size and therefore choose the appropriate field E and flow rate Q. Therefore the apparatus is a true "primary standard generator" in the field of submicron particles, with the advantage of being able to descend to particle sizes of approximately 1 nanometer, due to the dynamic confinement preventing losses by scattering on walls, which has not been possible with any hitherto known system.

I claim:

1. Electrical mobility selector of aerosol particles contained in an atmosphere, comprising a first and a second spaced, parallel, coaxial conductive disks defining a first space therebetween, an electrical field E being established between the disks by raising the disks to different potentials, the first space between the two disks communicating with the atmosphere to be examined through an annular slot of radius $r_1$ made in the first disk, a central intake being provided in the first disk for bringing about a circulation in said space, as from the periphery of the disks, of a stable, centripetal, laminar filtered air flow, the second disk being provided with an annular opening of mean radius $r_2$ ($r_2$<$r_1$), said selector also comprising:

a third disk facing the second disk and defining a second Space therebetween, means for injecting, into the second space between the second and third disks, a radial, laminar, filtered air flow from the periphery of said second and third disks, and a central pipe fixed to the third disk by which the particles are discharged to the outside of the selector.

2. Selector according to claim 1, means being provided for establishing between the second and third disks an auxiliary electrical field $\vec{E}'$ making it possible to "detach" the selected particles through the annular opening from the surface with which they can be in contact.

3. Selector according to claim 1, the annular opening being reduced to a single, central extraction orifice.

4. Selector according to claim 2, wherein the auxiliary electrical field $\vec{E}'$ is dependent on the electrical field $\vec{E}$.

* * * * *